United States Patent
Gut et al.

(10) Patent No.: US 6,303,298 B1
(45) Date of Patent: *Oct. 16, 2001

(54) TWO-STEP METHOD OF DNA AMPLIFICATION FOR MALDI-TOF MEASUREMENT

(75) Inventors: Ivo Glynne Gut, Berlin; Jochen Franzen, Bremen, both of (DE)

(73) Assignee: Bruker Daltonik GmbH, Bremen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/036,279

(22) Filed: Mar. 6, 1998

(30) Foreign Application Priority Data

Mar. 12, 1997 (DE) .............................................. 197 10 166

(51) Int. Cl.⁷ .............................. C12Q 1/68; C07H 21/04; C07H 21/00; G01N 24/00
(52) U.S. Cl. .............................. 435/6; 435/91.2; 435/403; 536/23.1; 536/24.33; 536/25.32; 436/173
(58) Field of Search .................................. 435/91.2, 403; 536/23.1, 24.33, 25.33; 436/173

(56) References Cited

U.S. PATENT DOCUMENTS

| 5,503,980 | * | 4/1996 | Cantor | 435/6 |
| 5,547,835 | * | 8/1996 | Koster | 435/6 |
| 5,705,621 | * | 1/1998 | Ravikumar | 536/23.1 |

FOREIGN PATENT DOCUMENTS

| 19543065 | 5/1997 | (DE) | C12Q/1/68 |
| 19643921 | 5/1997 | (DE) | G01N/27/68 |
| 9416101 | 7/1994 | (WO) . | |
| WO9506752 | 3/1995 | (WO) | C12Q/1/68 |
| 9514108 | 5/1995 | (WO) . | |
| 9627681 | 9/1996 | (WO) | C12Q/1/68 |
| 9637630 | 11/1996 | (WO) . | |

OTHER PUBLICATIONS

C.W. Siegert et al., Matrix–Assisted Laser Desorption/Ionization Time–of–Flight Mass Spectrometry for the Detection of Polymerase Chain Reaction Products Containing 7–Deazapurine Moieties, Analytical Biochemistry 243, 55–65 (1996) Article No. 0481.

M.J. Doktycz et al., Analysis of Polymerase Chain Reaction–Amplificated DNA Products by Mass spectrometry Using Matrix–Assisted Laser Desorption and Electrospray: Current Status, Analytical Biochemistry 230, pp. 205–214 (1995).

Parker et al. The oligomer extension "hot blot": a rapid alternative to southern blots for analyzing polymerase chain reaction products, Biotechniques, vol. 10(1), p. 94–101, 1991.*

* cited by examiner

Primary Examiner—Stephanie W. Zitomer
Assistant Examiner—Joyce Tung

(57) ABSTRACT

The invention referres to a method for the preparation and selective replication of deoxyribonucleic acid (DNA) from biomaterial using PCR (polymerase chain reaction) for the analysis in time-of-flight mass spectrometers (TOF) with matrix-assisted laser desorption and ionization (MALDI) for determining specific genetic features in biomaterial. The invention consists, in a first step, of replicating the selected DNA segments by the PCR method in the usual unmodified fashion, and in a further enzymatic replication process, to replicate the DNA segments using modified substrates (the nucleic acids used for PCR) and specially prepared primers to such DNA analogs as are especially suitable for ionization by MALDI. Preparation of the primers particularly consists of introducing a charged group, which improves the ionization, and modification of the substrates is used to neutralize the negative charge on the phosphoric acid group of the DNA backbone. It is especially practical to immobilize the DNA on a surface for the fmal enzymatic reduplication process, for example on a prepared MALDI layer located on magnetic beads. In the final reduplication process, extremely little reagent is used, thus it is also possible in terms of low cost to use isotope-enriched material here in order to increase the mass resolving power.

13 Claims, 1 Drawing Sheet

TWO-STEP METHOD OF DNA AMPLIFICATION FOR MALDI-TOF MEASUREMENT

The invention referres to a method for the preparation and selective replication of deoxyribonucleic acid (DNA) from biomaterial using PCR (polymerase chain reaction) for the analysis in time-of-flight mass spectrometers TOF) with matrix-assisted laser desorption and ionization (MALDI) for determining specific genetic features in biomaterial.

The invention consists, in a first step, of replicating the selected DNA segments by the PCR method in the usual unmodified fashion, and in a further enzymatic replication process, to replicate the DNA segments using modified substrates (the nucleic acids used for PCR) and specially prepared primers to such DNA analogs as are especially suitable for ionization by MALDI. Preparation of the primers particularly consists of introducing a charged group, which improves the ionization, and modification of the substrates is used to neutralize the negative charge on the phosphoric acid group of the DNA backbone. It is especially practical to immobilize the DNA on a surface for the final enzymatic reduplication process, for example on a prepared MALDI layer located on magnetic beads. In the final reduplication process, extremely little reagent is used, thus it is also possible in terms of low cost to use isotope-enriched material here in order to increase the mass resolving power.

PRIOR ART

"DNA fingerprinting" or "DNA typing" is currently revolutionizing the individual identification and characterization of hereditary factors (including factors for disease) in humans, animals, and plants. It is ultimately based on the determination of the molecular weight of replicated, highly variable DNA segments ("hypervariable DNA regions", "polymorphic DNA segments"), such as so-called microsatellites (also known as STR=short tandem repeats), which consist of a varying number of repetitions of short sequences of two to five nucleotides, but also of other polymorphic forms, such as those of 2-allelic polymorphisms based on point mutations. The sizes of the amplified DNA segments are currently still measured by the slow and not completely automatable method of polyacrylamide gel electrophoresis (PAGE). All of these types of genetic typing could however be approached considerably better and more exactly using mass spectrometric measurements of the molecular weights. For the latter type of polymorphisms, a particular type of sample preparation using a mutation-dependent slicing of the DNA is required.

Medicine today is aware of far more than 3,000 monogenous diseases which can be teed back to such mutated changes of individual genes, while the still more widespread polygenous diseases have not yet been researched to any extent It can be expected that we will have identified all genes in five years, all mutations in ten years. Today, about 10,000 microsatelites are already known for humans, and it can be expected that there are more than ten times as many.

It is known that DNA consists of two complementary chains of four alternating nucleotides, the sequence of which forms the genetic code. Each nucleotide consists of a sugar (ribose), a phosphoric acid group and a base. Two bases each are complementary to one another. Sugar and phosphoric acid form the continuous chain of DNA (or the so-called backbone), the four characteristic bases are respective lateral branches attached to the sugar group. Both complementary chains of DNA are joined in the form of a double helix, whereby two complementary nucleotides are joined to one another via hydrogen bridges between the bases.

The basis for the fingerprint analysis method is the PCR ("polymerase chain reaction"), a simple in-vitro replication method for specifically selectable DNA pieces, first developed in 1983 by K. B. Mullis (Nobel Prize 1993), which, after the introduction of thermally stable polymerases, made an unprecedented conquest of genetic laboratories. The gel-electrophoretic analyses of minimal initial amounts of DNA, which have become feasible today due to this method, are performed on a PAGE basis (PAGE=polyacrylamide gel electrophoresis). However, specialists see no future in this type of analysis since it consistently eludes an often-attempted automation due to various types of frequently occurring artefacts and therefore requires a great number of personnel. In addition, it is slow and also quite expensive, due to its relatively heavy use of expensive reagents. This method was a pioneering procedure, though it has proven to be a bottleneck for further broadening of the method.

One method which shows promise on many levels is capillary electrophoresis, with a multiple of capillaries, though it only just starts to market with industrially produced commercial units.

PCR is the targeted replication of a precisely defined piece of double-stranded DNA. The DNA segment is selected by a so-called pair of primers, two DNA pieces with about 20 bases length apiece, which (described somewhat briefly and simply) encode both ends of the selected DNA piece. Replication is performed by an enzyme called polymerase, which represents a chemical factory in a molecule, in a simple thermal cycle. The PCR reaction takes place in aqueous solution in which a few molecules of the original DNA and sufficient quantities of polymerase, primers, nucleic acids and stabilizers are present The thermal cycles consist for example in melting of the double helix at 92° C., hybridization of the primer at 55° C., and reconstitution of the primers by prolongation to form the missing complement of the double helix through attachment of substrates by the polymerase at 72° C. In every thermal cycle, the amount of the selected DNA segments thus is doubled in principle. Therefore, over 30 cycles, around one billion DNA segments are generated from one single double-strand of DNA as original material. (In a more exact description, both primers hybridize on the two different strands of the DNA and the shortening to the DNA segment between the primers only occurs statistically during further replication).

Under optimal conditions, the polymerase can attach about 500 to 1,000 bases per second to the primer. If there is a sufficient surplus of primers, polymerase and nucleotide substrates, the cycle period is practically only dependent on the rate of heating up and cooling down, which by itself depends upon the volume of liquid, the volume of the container, the thermal conductivity, and so on. For every temperature level only a few seconds are necessary in principle.

The primers are normally a part of the replicated DNA segments. Therefore chemical groups, which may be used for later detection (such as fluorescent groups), can be attached to the artificially produced primers.

By use of only one primer pair, uniform DNA segments can be replicated. However, if several different primer pairs are added at the same time, several DNA segments are replicated in the same PCR process ("multiplexed PCR").

This type of multiplexed PCR is frequently used and often has special advantages. For so-called "fingerprinting", for identification of individuals through DNA segments of variable length (method of "VNTR=Variable Number of Tandem Repeats" or "AMP-FLP=Amplified Fragment Length Polymorphism"), this makes the analyses faster. By selection of the primers which determine the average molecular weight of the DNA segments, the variations in molecular weight of DNA segments formed by the various primer pairs can be tailored to never or only seldomly overlap. This type of multiplex PCR requires an analyzer capable of simultaneous measurement of a large range of molecular weights.

The method has particular advantages in the identification of infectious organisms, since 20 types of bacteria (or viruses, yeasts, molds) can be detected at the same time, for example, with a single PCR replication procedure.

It must be expected that mass spectrometric measurements of molecular weight will be possible with much greater sensitivity and much higher velocities than with gel electrophoresis. The currently rapid progress in MALDI technology is leading to a high degree of automation for sample ionization and to brief analysis times per sample. In this way, molecular weight determinations of even very large analyte molecules in quantities of several hundred attomol within measurement periods of a few seconds will become possible. Many thousand of samples may be stored on one sample support Automation of the mass spectrometric analysis procedure with a high density of samples, and the use of massive-parallel preparation of several ten thousands of samples per day, opens the method towards high sample throughput.

Mass spectrometers using MALDI or ESI technology (ESI=electrospray ionization) are already been used for the sequencing of DNA according to the Sanger scheme utilizing PCR methods, cf. PCT/US94/00193.

An overview of the status of mass spectrometric DNA analyses is provided by the article "Analysis of Polymerase Chain Reaction-Amplified DNA Products by Mass Spectrometry Using Matrix-Assisted Laser Desorption and Electrospray: Current Status") by M. J. Doktycz et al., Analytical Biochemistry 230, 205–214 (1995).

In the literature, the following problems in the ionization of DNA using the MALDI process are described:
(1) Low sensitivity. It is at least two orders of magnitude less than for proteins.
(2) Adduct formation with statistically alternating deposition of cations, especially of ubiquitous alkali ions and of matrix ions from the MALDI preparation. These lead to inferior mass resolution and inferior mass accuracy.
(3) Fragmentation of instable DNA molecules. These lead to undesirable fragment ions which make multiplexed PCR, for example, impossible.

Today, mass spectrometric DNA analysis is therefore limited to DNA lengths of about 40 to 60 bases. This limit is given by the fact that the accuracy of the mass determination above this limit does no longer allow to measure the molecular weight precisely to one nucleotide. The mass resolution is even more greatly limited.

In PCT patent PCT/GB96/00476 (WO 96/27681), a method is described as to how DNA analogs can be produced which are much better suited for the MALDI process. Electrically charged groups can be incorporated into the primers for MALDI mass spectrometry, which support the MALDI process of ionization in such a way that a very high ion yield is achieved, and thus a very high sensitivity. On the other hand, the negative groups of the DNA backbone are neutralized, which not only improves stability, but also especially suppresses adduct formation.

This neutralization can be achieved in such a way that nucleotides are already used for PCR replication, for which the negatively charged OH group on the phosphoric acid is replaced by an SH group. Once the PCR replication is complete, the proton of the SH group may be specifically replaced by an alkylation reaction and thus neutral the backbone. When suitable polymerases are used, the PCR reaction also takes place with SH-nucleotide substrates, however the danger exists of increased error rates for these reactions.

It would be even more elegant to introduce neutralized (such as alkylated or fluoroalkylated) nucleotides into the PCR reaction from the beginning. However, the error rate for the PCR reaction then increases so significantly that a clean replication is no longer possible.

The replicated DNA segments to be measured must then be cleaned of all reagents and buffers used in the PCR reactions before mass spectrometric analysis by MALDI ionization. In biochemistry and molecular genetics, so-called microtiter (or microwell, microvial) plates have become established for parallel (synchronous) preparation of many samples. There are already commercially available sample preparation systems which operate using microtiter plates. These originally held 96 small reaction containers in a 9 mm grid on a 72 by 108 millimeter usable area. Today, plates of the same size with 384 reaction containers molded into the plastic in a 4.5 mm grid have become established. Plates with 864 reaction vials in a 3 mm grid or even 1536 reaction vials in a 2.25 mm grid are soon to come.

The preparation of samples frequently known as "massive-parallel", such according to molecular genetics, consists on the one hand in working not only with one such microtiter plate, but also with a large number of such plates in parallel. For example, with simultaneous treatment of 120 such 364-vial plates in a single PCR apparatus, more than 46,000 DNA samples could be replicated at the same time over a period of about 3 hours by a billion times each. On the other hand, it must be expected that the PCR time for a billion-fold replication will be reduced to less than 10 minutes with minaturized reaction systems in the near future, whereby more than a thousand such reaction systems can be placed on the surface of a current microtiter plate by the reduction of reaction systems to only a few microliters content For example, 1,536 sample vials in a 2.25 mm grid may become available on the surface of current microtiter plates. The introduction of microsystem technology can lead to further reductions. Synchronous transfer of all samples from these microreactors to MALDI carrier plates will follow.

MALDI (matrix-assisted laser desorption and ionization) is an ionization method for macromolecular analyte substances on surfaces. The analyte substances are applied together with suitable matrix substances of average size in a solution onto a surface, dried there and irradiated with a laser pulse of a few nanoseconds duration. A small amount of matrix substance is vaporized, some molecules of which as ions. The very dilute analyte substance, the molecules of which are singled out in the dilution, is also vaporized, even if its vapor pressure normally is insufficient for vaporization. The relatively small ions of the matrix substance react with the large molecules of the analyte substance with the result that the analyte substance molecules remain behind as ions due to proton transfer.

A particular type of MALDI makes use of mixed preparations in amorphous solutions. Matrix substances may thus be applied as a solid solution in a lacquer layer of explosive material, for example of nitrocellulose. This lacquer layer is highly adsorptive and can bond large biomolecules to its surface. This type of MALDI preparation has advantages: it is easy to prepare ahead and the analyte molecules may be applied very easily.

For the relatively high mass range of about 100,000 atomic mass units, i.e. approximately that of single-stranded DNA with about 250 bases, yet another effect must expectedly occur which limits the mass resolving power and is not yet even described in current literature regarding DNA analyses. Through the isotopes of naturally occuring elements, here primarily through the isotopes of carbon with 98.9% $^{12}C$ and 1.1% $^{13}C$, isotope distributions of the molecular ions result, the isotopic pattern of which can no longer be mass spectrometrically resolved. A single, relatively wide peak thereby results which limits the mass resolving power. For a DNA with a molecular weight of 100,000 atomic mass units, it has a half-value width of about 20 atomic mass units, corresponding to a resolution of about R=5,000.

The nucleotides of the DNA are only slightly different from the masses which range differentially from 9 to 20 atomic mass units between the four nucleotides. If very precise mass determinations are desired, for example for the quick clarification of point mutations, this half-value width of the isotope distribution is already an obstacle. High accuracies for mass determination may be achieved, for example, by using time-of-flight mass spectrometers with reflectors, or also particularly by using cyclotron resonance mass spectrometers with Fourier analysis of the vibrations.

One obvious solution for this problem is the application of isotope-enriched reagents, however Gus the high costs of such a solution are generally prohibitive to this application. In the PCR technology standardly applied, the reagents are mixed with primers and polymerases and applied with a great surplus, making it hardly possible to recover the surplus, valuable substrate solutions.

OBJECTIVE OF THE INVENTION

It is the objective of the invention to find an inexpensive PCR method by which sufficient amounts of DNA segments with neutral backbone and with charge-tags can be produced, washed and introduced into a MALDI preparation for the MALDI process of mass spectrometric measurement, as simply and sufficiently free of error as possible.

DESCRIPTION OF THE INVENTION

It is the basic idea of the invention to replicate the DNA strand with the genetic feature, in a first step of the method, first with a normal, safely functioning PCR process frequently enough into unmodified DNA segments, then to wash and thereby free them of reagents previously used for the PCR reaction, and then, in a further step of the method, to use a single PCR reaction cycle for the enzymatic reduplication of DNA with modified substrates which leads, for instance according to methods outlined in PCT/GB96/00476, to a modified, easily neutralizable DNA variant or even directly to a neutralized DNA analog. In other words, the substrates are conducive to the formation of electrically neutral linkages. Even if a few percent of faulty DNA copies are formed in this final duplication reaction, the subsequent mass spectrometric analysis is not endangered by these small amounts of admixtures.

It is a further idea of this invention to immobilize the generated DNA segments after normal PCR replication onto a surface for the process of washing. Immobilization can take place through hybridization onto a DNA piece which is attached to a surface. Since single strands are necessary for this which are already unavoidably hybridized with the primers of the first-stage PCR after the melting and cooling, it is a further idea of the invention to use a primer for this which attaches to another (nested) location in the DNA segment to be measured, most favorably beside the primer of the first step.

It is a further idea of the invention that this DNA piece be a primer which is used for the final enzymatic replication of the DNA segment. This primer may already be modified for the neutralization or already neutralized.

Through the enzymatic replication process of completion of the DNA segment with modified substrates, a double-stranded DNA (double helix) results, one strand of which consists of a modified, desirable DNA analog which is prepared for neutralization or is already neutral, and the other strand of which consists of a normal, non-modified DNA. The strand of desirable DNA analogs is a prolongation of the primer attached onto the surface. If the double helix is separated ("melted") by an increase in temperature, the unattached strands with non-modified DNA may be washed away. The washed, desirable DNA analog may then be neutralized (if not yet neutral), detached from the surface, applied to a MALDI layer and analyzed.

It is a further idea of the invention to use the surfaces of exchangeable particles, particularly of small magnetic beads, for the attachment of primers. These beads can be moved, added or removed in a suitable fashion using magnetic tweezers.

It is a further basic idea of the invention to have already applied a MALDI foundation to the surfaces for bonding the DNA segments so that these surfaces are immediately available for the MALDI process. The primers are therefore attached to the MALDI layer, for example the surface of a nitrocellulose lacquer layer which has sufficient free OH positions for bonds. These may be smooth surfaces or also particle surfaces, particularly those of magnetic beads.

The latter may be transferred to a sample carrier with magnetic tools and be subjected there to the MALDI process.

The demand for reagents for the final enzymatic reduplication is extraordinarily low. Since the primers for this step are attached to the surface, only a solution with polymerase and modified substrates which contain no specific reagents (primers) must be added. The surplus solution thus can be easily recovered after production of the modified DNA strands.

It is therefore a further idea of the invention to use isotope-enriched reagents for mass determinations of high accuracy in order to increase the mass spectrometric resolution. Due to the minimal consumption and the recovery of excess solution, the price of these isotope-enriched reagents remains reasonable. Application of carbon, enriched to 99.8% $^{12}C$, would reduce the half-value width of the isotope pattern to less than 5 mass units. In this way mass determination is possible which is accurate to about one mass unit The four nucleotides have different masses; they differ by a maximum of almost 10%. Therefore, the number of bases cannot be determined from a molecular weight determination with a relatively large number of nucleotides, since the ratio of nucleotides to one another is unknown. However, it may be possible in the future to generate a PCR copy in the final stage using a "universal" base. Such a universal base is a base which is complementary to all four natural bases and is therefore incorporated at all positions by the polymerase. It is now a further idea of this invention to use only this universal base in the final stage of the PCR. The result is a DNA analog which contains only this one single base type, i.e. this universal base, although it corresponds in its length (meaning: in the number of its bases) exactly to the original The mass spectrometric determination of the molecular weight then provides very precisely the number of bases for this DNA analog and therefore the original DNA section between the primers.

The "universal base" as a basic idea may not be verified because this base must connect to bases with two hydrogen bridges and to those with three hydrogen bridges. It may however be possible to create single bases or base pairs of exactly the same molecular weight, for instance by modifying the four natural DNA bases. These bases of exactly the same weight may serve the same purpose as the universal base. The replacement of PCR reagents with modified substrates and primers enhances the nucleotides ability to be measured as modified copy reaction product using mass spectrometry. A preferred embodiment of the invention uses modification steps that are known in the prior art. These steps include the elimination of the negative charges of the DNA sugar-phosphate backbone by use of alkylated phosphorothioates and/or the introduction of a charge tag to controllably ionize the product DNA molecule. Other prior art methods of modification may also provide the desired results and, when used in the manner described herein, are considered to be within the scope of the present invention. Such modifications generally provide the modified segments with charge characteristics beneficial to MALDI analysis.

ESPECIALLY FAVORABLE EMBODIMENTS

The method is particularly used for so-called "fingerprinting", in which microsatellites (or STR=short tandem repeats) of variable length are measured. Their length can be easily determined via mass spectrometric molecular weight determination. As pair of primers, copies of bilaterally adjacent DNA regions of minimal variability are used.

The point mutations, more difficult to measure directly, can be cut using biochemical agents at the point of mutation, for example by hybridization with subsequent enzymatic slicing (or with subsequent chemical treatment) specifically into two DNA partial sections, and thereby reconverted into analyte molecules, the characteristic molecular weight of which is easy to measure.

In an especially preferable method, about 600 million to 60 billion DNA segments are first generated in the standard manner from the DNA isolated from a biosample with a minimum of 10 and a maximum of 1,000 cells (for example about 100 cells from a hair root) by respective doubling in 26 PCR cycles, which corresponds to about 10 to 1,000 femtomol of DNA segments. The final cycles are depicted schematically in FIGS. 1, 2 and 3, whereby the lengths of the DNA segments are shown greatly reduced, however. The primers normally have lengths of about 20 bases.

Figure 1:
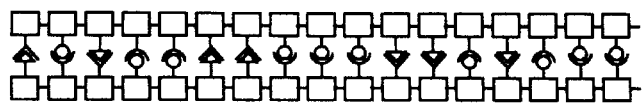
FIG. 1 shows a simplified schematic of a DNA double strand. The four nucleotides encode the gene in the known manner, while complementary bases are each coupled to one another and form the helix-shaped twisted double strand. The twisted helix structure is not shown.
Figure 2:
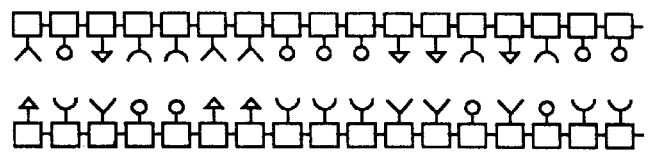
In FIG. 2, the DNA from the simple schematic is "melted", and both individual strands are separated from one another. This occurs above about 90° C.

FIG. 1 shows a DNA double strand, shortened by selection with the primers, which has been completed at about 70° C. by the polymerase. FIG. 2 shows the two single strands melted at about 90° C., onto which the terminal primers are attached at about 55° C. and shown in FIG. 3. The primers, added to the mixture of polymerase and substrate, determine the selection of the DNA piece which is then replicated. The substrate consists in known manner of the four triphosphate nucleotides, from which the nucleotides are incorporated by the polymerase piece by piece onto the primer as a complementary copy of the strand, until the end of the complementary strand is reached. Two DNA segments joined in the form of a double helix result, as they are shown in principle (however only in a planar arrangement, not in the form of a twisted double helix) in FIG. 1.

Figure 3:
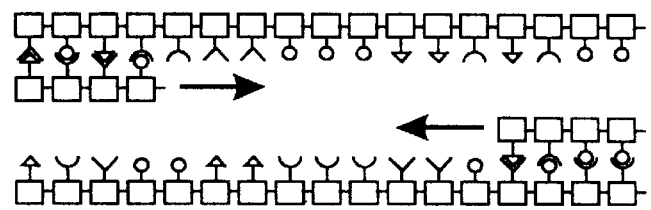
In FIG. 3, both individual strands are hybridized with both primers. The primers represent a vector for the polymerase which determines the direction of build-up. These directions are symbolized by arrows. Hybridization takes place at about 55° C., and at about 70° C. the polymerase operates at its optimum temperature and regenerates the double strands through the incorporation of nucleotides from the substrates. Two double strands then result.

After these 26 cycles, a magnetic bead which contains a precisely determined amount (for example five femtomol) of a modified second-stage primer on its surface, is added to the solution in which the DNA is found in single-strand condition in FIG. 3 after cooling down from 90° C. to 55° C. This primer is made up of modified, backbone-neutralized DNA and contains a chemical group with a positive charge ("charge tag"), for example by attachment of a quaternary ammonium group.

A minuscule magnetic bead of only three micrometers diameter can bind about 10 to 100 femtomol to its surface. The bond to the surface is such that it may be easily dissolved, for example by simply changing the pH value of the solution, or reactively, with a cutting enzyme. The second-stage primer has a code which corresponds complementarily to a DNA piece beside the already hybridized primer of the first PCR step.

Figure 4:
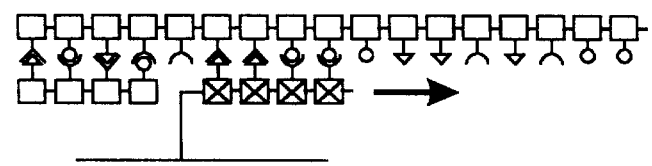
FIG. 4 shows the hybridization of a single strand at about 55° C. with a second primer, which is fixated onto a surface. Again, the direction of build-up is symbolized by an arrow. The primer consists of modified DNA, symbolized by the crosses.

The DNA single strands found in the solution now hybridize onto the firmly attached second-stage primer, as shown in FIG. 4. Here only one of the complementary DNA strands is used. Predetermined amounts are bonded to DNA by the dosage of fixated primers, for example five femtomol, so that a specific signal size is achieved in the mass spectrometer. The surplus DNA and the former PCR reagent solution are now washed away and the solution of polymerase and substrates with modified nucleotides is added. This solution contains no analysis-specific primers and may therefore be recovered and used again. The nucleotides of this solution are neutralized on a phosphoric acid group, for example by alkylation. Other means of neutralization are known and are equally applicable hereto.

Figure 5:
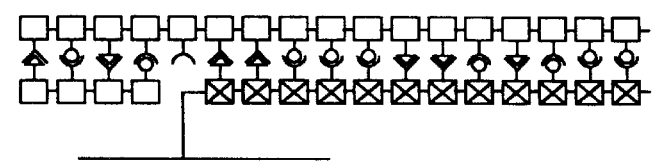
FIG. 5 shows the double strand completed by the work of the polymerase using modified substrate at about 70° C. The new part consists completely of modified DNA, symbolized by the crosses.

Heating up to about 70° C. now leads to completion of the DNA strand, whereby a strand of modified DNA is formed as a copy which forms a double strand with the unmodified DNA copy original, as schematically depicted in FIG. 5. This enzymatic reduplication process (Oust one cycle of a PCR reaction) does not proceed completely without error due to the modification of the substrates; a few percent of wrong DNA are formed which does not however disturb the mass spectrometric detection since the signal must have a preprogrammed heights The excess solution for the PCR process can be drawn off again and reused since it is essentially unchanged.

Figure 6:
FIG. 6 represents the melted, single strand of modified DNA attached to the surface. The second, unmodified strand has been removed by washing. The modified single strand may be returned to solution by detaching the bond to the surface and applying it to a MALDI layer.

These DNA double strands, attached firmly to the surface, may now be melted in a washing liquid at about 90° C., whereupon the unattached and unmodified DNA strands are washed away. The modified DNA single strands remain behind. These are attached to the surface as shown schematically in FIG. 6. In a further stage, the individual strands are detached from the surface by a cutting enzyme (or by a simple change in the pH value, for example by addition of some ammonia), and applied to a MALDI layer with a micropipette. The DNA pieces are adsorbed by the MALDI layer. Once the solution has dried, this layer may be washed in order to rinse away remaining buffer salts and other components. The DNA sample spots are then ready for analysis in the mass spectrometer using ionization by bombardment with pulsed laser light.

This method of generating modified DNA only in the final stage, has the advantage of relatively great safety for the PCR reactions. If modified primers and modified substrates would be used from the beginning, errors would expectedly occur already in the first PCR generations in a few percent of the samples, which would then be exponentially reproduced over the further course of the PCR amplification and lead to false analysis results.

The advantage of using magnetic beads lies in the fact that all reactions may be carried out on the same microtiter plate, and that therefore one stage of pipette transfer is eliminated.

It is however not absolutely necessary to detach the DNA from the surface of the magnetic beads. If the modified primers are attached to an undissolved MALDI layer on the beads, the magnetic beads may be transferred with magnetic tweezers to the sample support of the mass spectrometer, glued or magnetically fixated there and subjected to the MALDI process. The undissolved MALDI layer may consist of cross-linked nitrocellulos, for example.

The method described may naturally be varied in many ways. Magnetic beads are thus not absolutely necessary for fixation. A second set of microtiter plates, for example, may be provided on the bottom of the microvials with immobilized second-stage primers. After normal PCR in a first set of microtiter plates, the solution is then transferred by pipette into the second set, and the washing and final stage of PCR is carried out in the microtiter plates of the second set.

It is sometimes necessary for DNA analysis to make very accurate mass determinations even in a high mass range. Here, the width of the mass peak prescribed by the isotope distribution is an obstacle. However, a solution of polymerase with isotope-enriched substrates may be used in this case. Since this solution can be reused and is consumed only extremely slowly, a minimal price for the individual analysis is achieved even at a high price for the reagents used.

On the other hand, it is often necessary to know the exact number of bases in a DNA segment determined by both primers, without knowing exactly the relative abundances of the four nucleotides in this segment. In this case, one single type of base can be used in the final PCR step which is incorporated complementarily into all four nucleotides of the original to be copied by the polymerase onto the second-stage primer. Then the copy consists only of this "universal base", which however occurs exactly as frequently as the four nucleotides of the original together. Since the mass of this universal base is known, the mass determination provides the exact number of bases for the original.

Instead of just one "universal base", also single bases of exactly the same molecular weight can serve the same purpose. These bases may be generated by modifying the natural DNA bases. Especially for purposes of sequencing according to one of the well-known schemes (such as the well-known Sanger method), for which the mass spectrometric method may also be used, the application of the "universal base" or of the bases with identical weight is advantageous. The application calibrates the base scale; the base scale is thereby no longer dependent on the incidental distribution of the four nucleotides in the DNA partial piece to be measured.

What is claimed is:

1. A method for PCR amplification of selected DNA segments and preparation of these samples for mass spectrometric analysis using matrix assisted laser desorption/ionization (MALDI), whereby the DNA is modified such that the DNA segments become fragmentation-stable, easy to ionize and inert against adduct formation in the MALDI process, comprising the following steps:

(1) amplifying DNA segments using unmodified primers and unmodified substrates by normal PCR to produce sufficient DNA segments for a subsequent MALDI analysis, (2) exposing the amplified DNA segments to a modified primer having a predetermined charge suitable for analysis using MALDI, and at least a first substrate suitable for forming electrically neutral linkages, wherein the modified primer bonds only to one strand of any given DNA segment, (3) performing at least one enzymatic replication with the modified primer and at least the first substrate to generate modified segments of DNA analogs, the replication proceeding such that modified DNA strands form double strands with unmodified DNA strands, (4) preparing MALDI sample spots containing the modified DNA segments on a sample support, and (5) analyzing the molecular weight of the DNA segments by MALDI mass spectrometry.

2. A method according to claim 1, wherein the modified primer provides a more positive charge to the DNA analog segments.

3. A method according to claim 2, wherein after step (3) the linkages in the DNA analog segments are neutralized.

4. A method according to claim 1 wherein, after step (1), at least one single-stranded DNA segment is immobilized at a surface before step (2).

5. A method according to claim 4, wherein the modified primer is attached to the surface and is used to immobilize the single-stranded DNA segments to the surface.

6. A method according to claim 5, wherein the surface-attached modified primer is not sequence-identical with one of the unmodified primers used in the first step.

7. A method according to claim 6, wherein the surface-attached modified primer hybridizes at a location of a single-stranded DNA segment adjacent to a hybridization location of one of the primers used in step (1).

8. A method according to claim 4, wherein immobilization at the surface takes place on a MALDI layer.

9. A method according to claim 4, wherein the immobilization takes place on the surface of exchangeable particles.

10. A method according to claim 9, wherein the immobilization takes place on the surface of magnetic beads.

11. A method according to claim 4, wherein a primer-free solution of polymerase, substrates and buffers is recovered and reused in step (1).

12. A method according to claim 4, further comprising exposing the amplified DNA segments to isotope-enriched substrates.

13. A method according to claim 1, wherein nucleotides of the same molecular weight are used as substrates in step (3).

* * * * *